United States Patent [19]

Wason et al.

[11] Patent Number: 5,676,932
[45] Date of Patent: Oct. 14, 1997

[54] SILICA ABRASIVE COMPOSITIONS

[75] Inventors: Satish Kumar Wason, Bel Air, Md.; David Earl Rice, Cincinnati, Ohio

[73] Assignee: J.M. Huber Corporation, Edison, N.J.

[21] Appl. No.: 593,175

[22] Filed: Feb. 1, 1996

Related U.S. Application Data

[63] Continuation of Ser. No. 432,695, May 2, 1995.

[51] Int. Cl.⁶ .................................................. A61K 7/16
[52] U.S. Cl. ................................................................ 424/49
[58] Field of Search ...................................... 424/49

[56] References Cited

U.S. PATENT DOCUMENTS

| | | | |
|---|---|---|---|
| 3,577,521 | 5/1971 | Scheller et al. | 424/55 |
| 3,893,840 | 7/1975 | Wason | 423/339 |
| 3,937,807 | 2/1976 | Haefele | 424/52 |
| 3,959,458 | 5/1976 | Agricola et al. | 424/52 |
| 3,960,586 | 6/1976 | Wason | 106/309 |
| 3,967,563 | 7/1976 | Wason | 106/309 |
| 3,988,162 | 10/1976 | Wason | 424/49 |
| 4,051,234 | 9/1977 | Gieske et al. | 424/52 |
| 4,067,746 | 1/1978 | Wason et al. | 106/306 |
| 4,083,955 | 4/1978 | Grabenstetter et al. | 424/49 |
| 4,122,160 | 10/1978 | Wason | 424/49 |
| 4,122,161 | 10/1978 | Wason | 424/49 |
| 4,340,583 | 7/1982 | Wason | 424/52 |
| 4,420,312 | 12/1983 | Wason | 424/52 |
| 4,421,527 | 12/1983 | Wason | 424/52 |
| 4,618,488 | 10/1986 | Maeyama et al. | 424/49 |
| 4,632,826 | 12/1986 | Ploger et al. | 424/52 |
| 4,885,155 | 12/1989 | Parran, Jr. et al. | 424/52 |
| 4,992,251 | 2/1991 | Aldcroft et al. | 423/335 |
| 5,004,597 | 4/1991 | Majeti et al. | 424/52 |
| 5,035,879 | 7/1991 | Aldcroft et al. | 424/49 |
| 5,098,695 | 3/1992 | Newton et al. | 424/49 |
| 5,110,574 | 5/1992 | Reinhardt et al. | 423/335 |
| 5,124,143 | 6/1992 | Muhlemann et al. | 424/49 |
| 5,213,790 | 5/1993 | Lukacovic et al. | 424/52 |
| 5,279,815 | 1/1994 | Wason et al. | 424/52 |
| 5,281,410 | 1/1994 | Lukacovic et al. | 424/52 |

FOREIGN PATENT DOCUMENTS

WO 92/02454   2/1992   WIPO .

OTHER PUBLICATIONS

S.K. Wason—Cosmetic properties and structure of fine-particle synthetic precipitated silicas—J. Soc. Cosmet. Chem.—29, 497–521 (Aug. 1978).

*Primary Examiner*—Shelley A. Dodson
*Attorney, Agent, or Firm*—Lowe Price LeBlanc & Becker

[57] ABSTRACT

Oral compositions, such as oral gels and toothpastes, containing a novel abrasive.

10 Claims, No Drawings

SILICA ABRASIVE COMPOSITIONS

This application is a continuation of application Ser. No. 08/432,695 filed May 2, 1995.

TECHNICAL FIELD

This invention relates to dentifrice compositions containing such as toothpastes which provide improved oral cleaning.

BACKGROUND OF THE INVENTION

Synthetically produced precipitated silicas play an important role as an ingredient in many of today's toothpaste formulations. In addition to their cleaning ability, they are also relatively safe, nontoxic, and compatible with other toothpaste ingredients, including glycerin, sorbitol (or xylitol), thickening agents, detergents coloring and fragrance materials and, optionally, fluoride containing compositions.

Synthetic precipitated silicas are prepared by admixing alkaline silicate solutions with acids, stirring and then filtering out the precipitated silica. The resulting precipitate is next washed, dried and comminuted to desired size. When preparing synthetic precipitated silicas, the objective is to obtain silicas which provide maximal cleaning with minimal damage to oral tissue. Dental researchers are continually concerned with identifying precipitated silicas meeting these objectives.

Examples of precipitated silicas include U.S. Pat. No. 4,122,161 to Wason, Oct. 24, 1978, U.S. Pat. Nos. 4,992,251 and 5,035,879 to Aldcroft et at., Feb. 12, 1991 and Jul. 30, 1991 respectively, U.S. Pat. No. 5,098,695. to Newton et al., Mar. 24, 1992, and U.S. Pat. No. 5,279,815 to Wason et al., Jan. 18, 1994.

Moreover, various combinations of silicas have also been described in the art. Silica combinations involving compositions of differing particle sizes and specific surface areas are disclosed in U.S. Pat. No. 3,577,521 to Karlheinz Scheller et al., May 4, 1971 and U.S. Pat. No. 4,618,488 to Macyarea et at., Oct. 21, 1986, respectively. Similarly, U.S. Pat. No. 5,110,574 to Reinhardt et al., May 5, 1992 discloses combining thickener and polishing silicas to form silica compositions having oil absorption values of at least 200. Further examples of silica combinations include U.S. Pat. No. 5,124,143 to Muhlemann, Jun. 23, 1992 and U.S. Pat. No. 4,632,826 to Ploger et at., Dec. 30, 1986.

In spite of the many disclosures relating to compositions for oral cleaning and antiplaque activity, there is still a need for additional compositions providing improved pellicle cleaning with minimal abrasion. The present inventor has discovered abrasive compositions comprising silicas having particles of differing hardness values provide improved dental cleaning with minimal abrasion.

Accordingly, it is the object of the present invention to provide precipitated silica compositions exhibiting improved pellicle cleaning without a corresponding increase in dentin or enamel abrasion. Another object of the present invention is to provide an effective method for the prevention or removal tooth stains. A further object of the present invention is to provide an effective method for the prevention or removal of plaque. These and other objects will become readily apparent from the disclosure which follows.

SUMMARY OF THE INVENTION

The present invention relates to precipitated silica abrasive composition, comprising:

a.) a precipitated silica, comprising particles wherein said particles have:
  i.) a mean particle size of from about 5 to about 11 microns (s.d. <7);
  ii.) an Einlehner hardness of from about 0.8 to about 2.5 for abrasive to brass screen and from about 5 to about below 8 for abrasive to polyester screen;
  iii.) an oil absorption of from 95 ml/100 gm to about 135 ml/100 gm; and
  iv.) a radioactive dentin abrasion of from about 25 to about below 80; and b.) a precipitated silica, comprising particles wherein said particles have:
  i.) a mean particle size of from about 5 to about 11 microns (s.d. <7);
  ii.) an Einlehner hardness of from about 3 to about 8 for abrasive to brass screen and from 8 to about 11 for abrasive to polyester screen;
  iii.) an oil absorption of from about 70 ml/100 gm to about below 95 ml/100 gm; and
  iv) a radioactive dentin abrasion of from 80 to about 200 wherein at least about 70% of all of said particles have a diameter of below about 20 microns and wherein the pellicle cleaning ratio is from about 90 to about 135 and the radioactive dentin abrasion is from about 60 to about 100 with a pellicle cleaning ratio/radioactive dentin abrasion ratio of from about 1.25 to about 1.75 and wherein the ratio of the silica in a.) to the silica in b.) is from about 90:10 to about 40:60, respectively.

All levels and ratios are by weight of the total composition, unless otherwise indicated. PCR and RDA values are unitless. Additionally, all measurements are made at 25° C. unless otherwise specified.

The pH of the present herein described compositions range from about 4 to about 9.5, with the preferred pH being from about 6.5 to about 9.0 and the most preferred pH being 7.0 to about 8.5, as measured in a 5% aqueous slurry.

DETAILED DESCRIPTION OF THE INVENTION

The essential as well as optional components of the compositions of the present invention are described in the following paragraphs.

Abrasive

The precipitated silicas used to form the silica compositions of the present invention can be characterized as either Low Structure or Medium Structure silicas in accordance with the definitions set forth in the J. Soc. Cosmet. Chem. 29, 497–521 (August, 1978), and Pigment Handbook: Volume 1, Properties and Economics, Second Edition, Edited by Peter A. Lewis, John Wiley & Sons, Inc., 1988, p. 139–159 and are preferably characterized as synthetic hydrated amorphous silicas, also known as silicon dioxides or $SiO_2$. Further, these silicas may be characterized as having a BET surface area in the range of 50 to 250 $m^2/g$.

These compositions are further characterized as having a median average particle size ranging from about 5 microns to about 11 microns with at least 70% of the particle size distribution being less than 20 microns. The average particle size (mean value and median or 50%) is measured using a Microtrac II apparatus, Leeds and Northrup. Specifically, a laser beam is projected through a transparent cell which contains a stream of moving particles suspended in a liquid. Lights rays which strike the particles are scattered through angles which are inversely proportional to their sizes. The photodetector array measures the quantity of light at several predetermined angles. Electrical signals proportional to the measured light flux values are then processed by a microcomputer system to form a multi-channel histogram of the particle size distribution.

The precipitated silicas used to form the compositions of the present invention are further differentiated by means of their respective Einlehner hardness values, Radioactive Dentin Abrasion (RDA) values and oil absorption values.

Einlehner hardness values are measured using an Einlehner At-1000 Abrader to measure the softness of the silicas in the following manner: A Fourdrinier wire screen is weighed and exposed to the action of a 10% aqueous silica suspension for a certain length of time. The amount of abrasion is then determined as milligrams weight lost of the Fourdrinier wire screen per 100,000 revolutions. Brass Einlehner (BE) and Polyester Einlehner (PE) results are expressed in milligrams.

The RDA values are determined according to the method set forth by Hefferren, Journal of Dental Research, July-August 1976, pp. 563–573, and described in the Wason U.S. Pat. Nos. 4,340,583, 4,420,312 and 4,421,527, which publication and patents are incorporated herein by reference.

The precipitated silica compositions of the present invention may be characterized as having oil absorption values of less than 200 cc/100 g. Oil absorption value are measured using the ASTM rub-out method D281. Surface area is determined by the BET nitrogen adsorption method of Brunaur et at., J. Am. Chem. Soc., 60, 309 (1938). To measure brightness, fine powder materials that are pressed into a smooth surfaced pellet are evaluated using a Tectnidyne Brightimeter S-5/BC. This instrument has a dual beam optical system where the sample is illuminated at a angle of 45°, and the reflected light viewed at 0°. It conforms to TAPPI test methods T452 and T646, and ASTM Standard D985. A series of filters direct to reflected light of desired wavelengths to a photocell where it is converted to an output voltage. This signal is amplified and then processed by an internal microcomputer for display and printout.

Precipitation of the silicas of the present invention is accomplished in accordance with the general methods described, for example, in prior U.S. Pat. No. 3,893,840, issued Jul. 8, 1975, to Wason; U.S. Pat. No. 3,988,162, issued Oct. 26, 1976, to Wason, U.S. Pat. No. 4,067,746, issued Jan. 10, 1978, to Wason; and U.S. Pat. No. 4,340,583, issued Jul. 29, 1982, to Wason; all of which are herein incorporated by reference.

In one step of the process, a first precipitated silica suspension is prepared by varying precipitation reaction parameters in a manner, ordinarily, resulting in precipitated silicas having BE values in the range of from about 0.8 mg to about 2.5 mg and PE values in the range of about 5 mg to about below 8 mg, an RDA ranging from about 25 to about 80, and an oil absorption of from 95 ml/100 gm to about 135 ml/100 gm. Reaction parameters which affect the characteristics of the resultant silica include: the rate at which the various reactants are added; the levels of concentration of the various reactants; the reaction pH; the reaction temperature or the rate at which electrolytes are added.

In another step of the precipitation process, a second precipitated silica suspension is similarly prepared varying reaction parameters in a manner, ordinarily, resulting in precipitated silicas having BE values in the range of from about 3 mg to about 8 mg and PE values in the range of 8 mg to about 11 mg, an RDA ranging from about 81 to about 200, and an oil absorption of from about 70 ml/100 gm to about below 95 ml/100 gm.

Thereafter, the two precipitated silica suspensions can be combined, adjusting the pH to about 5.0. The combination suspension is filtered and then washed with water to remove salts from the filter cake. The filter cake is dried, preferably by conventional spray drying to produce a precipitated silica containing about 3% to 10% moisture. The precipitated silica combination is milled to a particle size in which 70% of the particle size distribution is below 20 microns. Alternatively, the silicas can be combined prior to incorporation into dentifrice compositions.

In addition to the above described essential components, the dentifrice compositions of the present invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, Apr. 2, 1991 to Majeti; U.S. Pat. No. 4,885,155, Dec. 5, 1989 to Parran, Jr. et al.; U.S. Pat. No. 3,959,458, May 25, 1976 to Agricola et al. and U.S. Pat. No. 3,937,807, Feb. 10, 1976 to Haefele, all being incorporated herein by reference.

The Pellicle Cleaning Ratio (PCR) of the inventive silica combination, which is a measurement of the cleaning characteristics of a dentifrice, ranges from 90 to 135 and preferably from 100 to 130 for the precipitated silica combination of the invention. The Radioactive Dentin Abrasion (P. DA) of the inventive silicas, which is a measurement of the abrasiveness of the precipitated silica combination when incorporated into a dentifrice, ranges from 60 to 10, preferably from 80 to 90.

The PCR (Pellicle Cleaning Ratio) cleaning values are determined by a slightly modified version of the PCR test described in "In Vitro Removal of Stain With Dentifrice", G. K. Stookey, T. A. Burkhard and B. R. Schemerhorn, J. Dental Research, 61, 1236–9, 1982. Cleaning is assessed in vitro by use of the modified pellicle cleaning ratio test. This test is identical to that described by Stookey et al. with the following modifications: (1) a clear artificial pellicle film is applied to bovine chips prior to application of the stained film, (2) solution heating is used rather than radiative heating during film application, (3) the number of brush strokes is reduced to 200 strokes and (4) the slurry concentration is 1 part dentifrice to 3 parts water.

The precipitated silica compositions of the present invention, when incorporated into a dentifrice composition further provide an improved PCR/RDA ratio. The PCR/RDA ratio is used to determine the relative ratio of cleaning and abrasion characteristics of a dentifrice formulation. Commercially available dentifrice formulations generally have a PCR/RDA ratio in the range of 0.5 to below 1.0. The precipitated silicas used in the compositions of the present invention provide PCR to RDA ratios to dentifrice formulations of greater than 1, usually in the range of 1.25 to 1.75, but more preferably in the range 1.6 to 1.75.

The abrasive, in the form of a precipitated silica compositions of the present invention, when incorporated into the compositions described herein, is present at a level of from about 6% to about 70%, preferably from about 15% to about 35% when the dentifrice is a toothpaste. Higher levels, as high as 95%, may be used if the composition is a toothpowder.

OPTIONAL COMPONENTS

Pharmaceutically Acceptable Carrier

The carrier for the components of the present compositions is optional and can be any dentifrice vehicle suitable for use in the oral cavity. Such carriers include the usual components of toothpastes, tooth powders, prophylaxis pastes, lozenges, gums and the like and are more fully described hereinafter. Toothpastes are the preferred systems.

Surfactants

One of the preferred optional agents of the present invention is a surfactant, preferably one selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate.

This surfactant can be present in the compositions of the present invention from about 0.1% to about 2.5%, preferably from about 0.3% to about 2.5% and most preferably from about 0.5% to about 2.0% by weight of the total composition.

Other suitable compatible surfactants can optionally be used along with the sarcosinate surfactant in the compositions of the present invention. Suitable optional surfactants are described more fully in U.S. Pat. No. 3,959,458, May 25, 1976 to Agricola et at.; U.S. Pat. No. 3,937,807, Feb. 10, 1976 to Haefele; and U.S. Pat. No. 4,051,234, Sep. 27, 1988 to Gieske et at. These patents are incorporated herein by reference.

Preferred anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be utilized.

Preferred cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., herein incorporated by reference, where said quaternary ammonium fluorides have detergent properties. Certain cationic surfactants can also act as germicides in the compositions disclosed herein. Cationic surfactants such as chlorhexadine, although suitable for use in the current invention, are not preferred due to their capacity to stain the oral cavity's hard tissues. Persons skilled in the art are aware of this possibility and should incorporate cationic surfactants only with this limitation in mind.

Preferred nonionic surfactants that can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic synthetic surfactants useful in the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Preferred betaine surfactants are disclosed in U.S. Pat. No. 5,180,577 to Polefka et at., issued Jan. 19, 1993. Typical alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramido propyl betaine.

Chelating agents

Another preferred optional agent is a chelating agent selected from the group consisting of tartaric acid and pharmaceutically-acceptable salts thereof, citric acid and alkali metal titrates and mixtures thereof. Chelating agents are able to complex calcium found in the cell walls of the bacteria. Chelating agents can also disrupt plaque by removing calcium from the calcium bridges which help hold this biomass intact. However, it is possible to use a chelating agent which has an affinity for calcium that is too high. This results in tooth demineralization and is contrary to the objects and intentions of the present invention.

Sodium and potassium titrate are the preferred alkali metal titrates, with sodium titrate being the most preferred. Also preferred is a citric acid/alkali metal citrate combination. Preferred herein are alkali metal salts of tartaric acid. Most preferred for use herein are disodium tartrate, dipotassium tartrate, sodium potassium tartrate, sodium hydrogen tartrate and potassium hydrogen tartrate. The amounts of chelating agent suitable for use in the present invention are about 0.1% to about 2.5%, preferably from about 0.5% to about 2.5% and more preferably from about 1.0% to about 2.5%. The tartaric acid salt chelating agent can be used alone or in combination with other optional chelating agents.

Other optional chelating agents can be used. Preferably these chelating agents have a calcium binding constant of about $10^1$ to $10^5$ provide improved cleaning with reduced plaque and calculus formation.

Another group of agents suitable for use as chelating agents in the present invention are the soluble pyrophosphates. The pyrophosphate salts used in the present compositions can be any of the alkali metal pyrophosphate salts. Specific salts include tetra alkali metal pyrophosphate, dialkali metal diacid pyrophosphate, trialkali metal monoacid pyrophosphate and mixtures thereof, wherein the alkali metals are preferably sodium or potassium. The salts are useful in both their hydrated and unhydrated forms. An effective amount of pyrophosphate salt useful in the present composition is generally enough to provide at least 1.0% pyrophosphate ion, preferably from about 1.5% to about 6%, more preferably from about 3.5% to about 6% of such ions. It is to be appreciated that the level of pyrophosphate ions is that capable of being provided to the composition (i.e., the theoretical amount at an appropriate pH) and that pyrophosphate forms other than $P_2O_7-4$ (e.g., $(HP_2O_7-3)$) may be present when a final product pH is established.

The pyrophosphate salts are described in more detail in Kirk & Othmer, *Encyclopedia of Chemical Technology*, Second Edition, Volume 15, Interscience Publishers (1968), incorporated herein by reference.

Still another possible group of chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 copolymers of maleic arthydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Other operative polymeric polycarboxylates include those such as the 1:1 copolymers of maleic arthydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. both patents are incorporated herein by reference, and include copolymers of maleic anhydride with styrene, isobutylene or ethyl vinyl ether, polyacrylic, polyitaconic and polymaleic acids, and sulfoacrylic oligomers of M.W. as low as 1,000 available as Uniroyal ND-2.

Flavoring agents can also be added to dentifrice compositions. Suitable flavoring agents include oil of Wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

It is common to have a water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et at. and U.S. Pat. No. 3,678,154, Jul. 18, 1972 to Widder et at., both being incorporated herein by reference. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxethyl cellulose and water soluble salts of cellulose ethers such as sodium carboxymethyl cellulose and sodium carboxymethyl hydroxethyl cellulose. Natural gums such as gum karaya, xanthan gun, gum arabic, and gum tragacanth can also be used. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Also desirable for inclusion in the compositions of the present invention are other stannous salts such as stannous pyrophosphate and stannous gluconate and antimicrobials such as quaternary ammonium salts, such as cetyl pyridinium chloride and tetradecylethyl pyridinium chloride, bis-biquanide salts, copper bisglycinate, nonionic anti microbial salts and flavor oils. Such agents are disclosed in U.S. Pat. No. 2,946,725, Jul. 26, 1960, to Norris et at. and U.S. Pat. No. 4,051,234, Sep. 27, 1977 to Gieske et at., incorporated herein by reference. Other optional components include buffering agents, bicarbonates, peroxides, nitrate salts such as sodium and potassium nitrate. These agents, if present, are included at levels of from about 0.01% to about 30%.

Other useful carriers include biphasic dentifrice formulations such as those disclosed in U.S. Pat. No. 5,213,790, issued May 23, 1993, U.S. Pat. No. 5,145,666, issued Sep. 8, 1992, and U.S. Pat. No. 5,281,410 issued Jan. 25, 1994 all to Lukacovic et al. and in U.S. Pat. Nos. 4,849,213 and 4,528,180 to Schaeffer the disclosures of which are incorporated by reference herein.

Suitable lozenge and chewing gum components are disclosed in U.S. Pat. No. 4,083,955, Apr. 11, 1978 to Grabenstetter et al., incorporated herein by reference.

EXAMPLES

The following examples further describe and demonstrate preferred embodiments within the scope of the present invention. The examples are given solely for illustration, and are not to be construed as limitation of this invention as many variations thereof are possible without departing from its spirit and scope.

Example I

A dentifrice composition of the present invention contains the following components as described below.

| Component | Wgt % |
|---|---|
| Sorbitol 70% soln | 24.200 |
| RO Water | 24.757 |
| Glycerin | 7.000 |
| Carboxymethyl Cellulose[1] | 0.500 |
| PEG 6 | 4.000 |
| Sodium Fluoride | 0.243 |
| Sodium Saccharine | 0.130 |
| Monosodium Phosphate | 0.415 |
| Trisodium Phosphate | 0.395 |
| Sodium Tartrate | 1.000 |
| TiO2 | 0.500 |
| Silica[2] | 35.000 |
| Sodium Lauroyl Sarcosinate (95% active) | 1.060 |
| Flavor | 0.800 |

[1] Supplied by Aqualon Company.
[2] The precipitated silica ingredient possesses the following characteristics: APS Mean Value = 8.5 microns; oil absorption = 103 cc/100 g; BE = 1.6; PE = 7; PCR = 106; RDA = 67.

The jacket temperature of a mixing tank is set to about 150° F. (65° C.) to about 160° F. (71° C.). The humectants and water are added to the mixing tank and agitation is started. When the temperature reaches approximately 120° F. (50° C.) fluoride, sweetening agents, buffering agents, chelant, coloring agents and titanium dioxide are added. Thickening agents are added to the abrasive and the resulting mixture is added to the mixing tank with high agitation. The surfactant is added to the combination and mixing is continued. The tank is cooled to 120° F. (50° C.) and the flavoring agents are added. Mixing is continued for approximately 5 minutes. The resulting composition will have a pH of about 7.

Example II

A dentifrice composition of the present invention contains the following components as described below.

| Component | Wgt % |
|---|---|
| Sorbitol 70% soln | 29.810 |
| RO Water | 24.757 |
| Glycerin | 7.000 |
| Carboxymethyl Cellulose[1] | 0.750 |
| PEG 6 | 4.000 |
| Sodium Fluoride | 0.243 |
| Sodium Saccharine | 0.130 |
| Monosodium Phosphate | 0.415 |
| Trisodium Phosphate | 0.395 |
| TiO2 | 0.500 |
| Silica[2] | 30.000 |
| Sodium Lauryl Sulfate | 1.200 |
| Flavor | 0.800 |

[1]Supplied by Aqualon Company.
[2]The precipitated silica ingredient possesses the following characteristics: APS Mean Value = 8.5 microns; oil absorption = 103 cc/100 g; BE = 1.6; PE = 7; PCR = 106; RDA = 67.

Example III

A gum composition of the present invention contains the following components as described below.

| Component | Weight % |
|---|---|
| Gum Base | 30.000 |
| 30 parts Estergum | |
| 45 parts Coumorone Resin | |
| 15 parts Dry Latex | |
| Silica[1] | 10.00 |
| Sugar | 40.000 |
| Corn Syrup | 18.175 |
| Sodium Lauroyl Sarcosinate | 0.075 |
| Sodium Tartrate | 0.250 |
| flavor | 1.500 |

[1]The precipitated silica ingredient possesses the following characteristics: APS Mean Value = 8.5; oil absorption = 101 cc/100 g; BE = 1.9; PE = 7.2.

What is claimed is:

1. A precipitated silica abrasive composition, comprising:
   a.) a precipitated silica, comprising particles wherein said particles have:
      i.) a mean particle size of from about 5 to about 11 microns (s.d. <9);
      ii.) an Einlehner hardness of from about 0.8 to about 2.5 for abrasive to brass screen and from about 5 to about below 8 for abrasive to polyester screen;
      iii.) an oil absorption of from about 95 ml/100 gm to about 135 ml/100 gm; and
      iv.) a radioactive dentin abrasion of from about 25 to about below 80; and
   b.) a precipitated silica, comprising particles wherein said particles have:
      i.) a mean particle size of from about 5 to about 11 microns (s.d. <9);
      ii.) an Einlehner hardness of from about 3 to about 8 for abrasive to brass screen and from 8 to about 11 for abrasive to polyester screen;
      iii.) an oil absorption of from about 70 ml/100 gm to about below 95 ml/100 gm; and
      iv) a radioactive dentin abrasion of from about 80 to about 200 wherein at least about 70% of all of said particles have a diameter of below about 25 microns and wherein the pellicle cleaning ratio is from about 90 to about 135 and the radioactive dentin abrasion is from about 60 to about 100 with a pellicle cleaning ratio/radioactive dentin abrasion ratio of from about 1.25 to about 1.75 and wherein the ratio of the silica in a.) to the silica in b.) is from about 90:10 to about 40:60, respectively.

2. A precipitated silica abrasive composition according to claim 1, wherein the pellicle cleaning ratio is from about 90 to about 135, the radioactive enamel abrasion is from about 2.5 to about 5 and wherein the pellicle cleaning ratio/ radioactive enamel abrasion ratio of said precipitated silica abrasive composition is greater than about 30.

3. A precipitated silica abrasive according to claim 2, wherein the ratio of said silicas is from about 80:20 to about 35:65.

4. A precipitated silica abrasive according to claim 3, wherein the pellicle cleaning ratio is from about 110 to about 135.

5. A precipitated silica abrasive according to claim 4, wherein the radioactive dentin abrasion is from about 65 to about 85.

6. A precipitated silica abrasive according to claim 5, wherein the pellicle cleaning ratio/radioactive dentin abrasion ratio of said abrasive is from about 1.60 to about 1.75.

7. A precipitated silica abrasive according to claim 6, wherein the radioactive enamel abrasion is from about 2.5 to about 3.5.

8. A precipitated silica abrasive according to claim 7, wherein the pellide cleaning ratio/radioactive enamel abrasion ratio of said abrasive is from about 35 to about 44.

9. A precipitated silica abrasive according to claim 8, wherein the radioactive dentin abrasion of the silica in a.) is from about 35 to 80.

10. A precipitated silica abrasive according to claim 9, wherein the radioactive dentin abrasion of the silica in b.) is from about 110 to about 200.

* * * * *